United States Patent [19]
Anderson

[11] Patent Number: 5,575,795
[45] Date of Patent: Nov. 19, 1996

[54] UMBILICAL CORD HOLDER

[75] Inventor: Sanford J. Anderson, Eden Prairie, Minn.

[73] Assignee: Minneapolis Children's Medical Center, Minneapolis, Minn.

[21] Appl. No.: 301,808

[22] Filed: Sep. 7, 1994

Related U.S. Application Data

[63] Continuation-in-part of Ser. No. 95,269, Jul. 21, 1993, Pat. No. 5,372,581.

[51] Int. Cl.⁶ ................................................. A61B 17/42
[52] U.S. Cl. ........................ 606/120; 606/151; 606/157
[58] Field of Search ................................ 606/120, 151, 606/157, 142; 251/4, 5, 6, 7, 8

[56] References Cited

U.S. PATENT DOCUMENTS

| | | |
|---|---|---|
| 3,344,785 | 10/1967 | Hamilton . |
| 3,965,896 | 6/1976 | Swank . |
| 3,976,080 | 8/1976 | Bornhorst et al. ................ 128/348 |
| 3,977,407 | 8/1976 | Coleman et al. ................. 128/348 |
| 4,447,235 | 5/1984 | Clarke . |
| 4,545,377 | 10/1985 | Cerwin et al. ................... 128/325 |
| 4,744,785 | 5/1988 | Rosenthal et al. . |
| 4,924,864 | 5/1990 | Danzig ............................ 606/142 |
| 5,053,025 | 10/1991 | Knippscheer . |
| 5,059,168 | 10/1991 | Stone . |
| 5,097,842 | 3/1992 | Bonn . |
| 5,114,672 | 5/1992 | Knippscheer et al. . |
| 5,415,665 | 5/1995 | Hessel et al. ..................... 606/120 |

FOREIGN PATENT DOCUMENTS

| | | | |
|---|---|---|---|
| 0972731 | 10/1964 | United Kingdom ............ | 606/158 |
| 2128478 | 5/1984 | United Kingdom ............ | 606/158 |

OTHER PUBLICATIONS

Sanford Anderson, MD et al., article entitled "Retrieval of Placental Blood from the Imbilical Vein to Determine Volume, Sterility, and Presence of Clot Formation", from *American Journal of Diseases of Children*, Jan., 1992, vol. 146.

Skolnick, article entitled "Transfusion Medicine Faces Time of Major Challenges and Changes", *Medical News & Perspectives JAMA*, Aug. 12, 1992, vol. 268, No. 6, pp. 697–701.

Primary Examiner—Corrine M. McDermott
Assistant Examiner—Cris L. Rodriguez
Attorney, Agent, or Firm—Merchant, Gould, Smith, Edell, Welter & Schmidt, P.A.

[57] ABSTRACT

The present invention relates to an apparatus and a method for the withdrawal of placental blood from an umbilical cord vein. More specifically, the apparatus has an umbilical cord holder for use while withdrawing placental blood. The umbilical cord holder has a curved trough with a first end, a second end, an open top, and a bottom surface. The trough is needle resistant and sized to hold an umbilical cord. A step that has first and second ends is operatively connected to the bottom surface of the trough. The stem allows a user to hold and maneuver the umbilical cord holder during use.

7 Claims, 5 Drawing Sheets

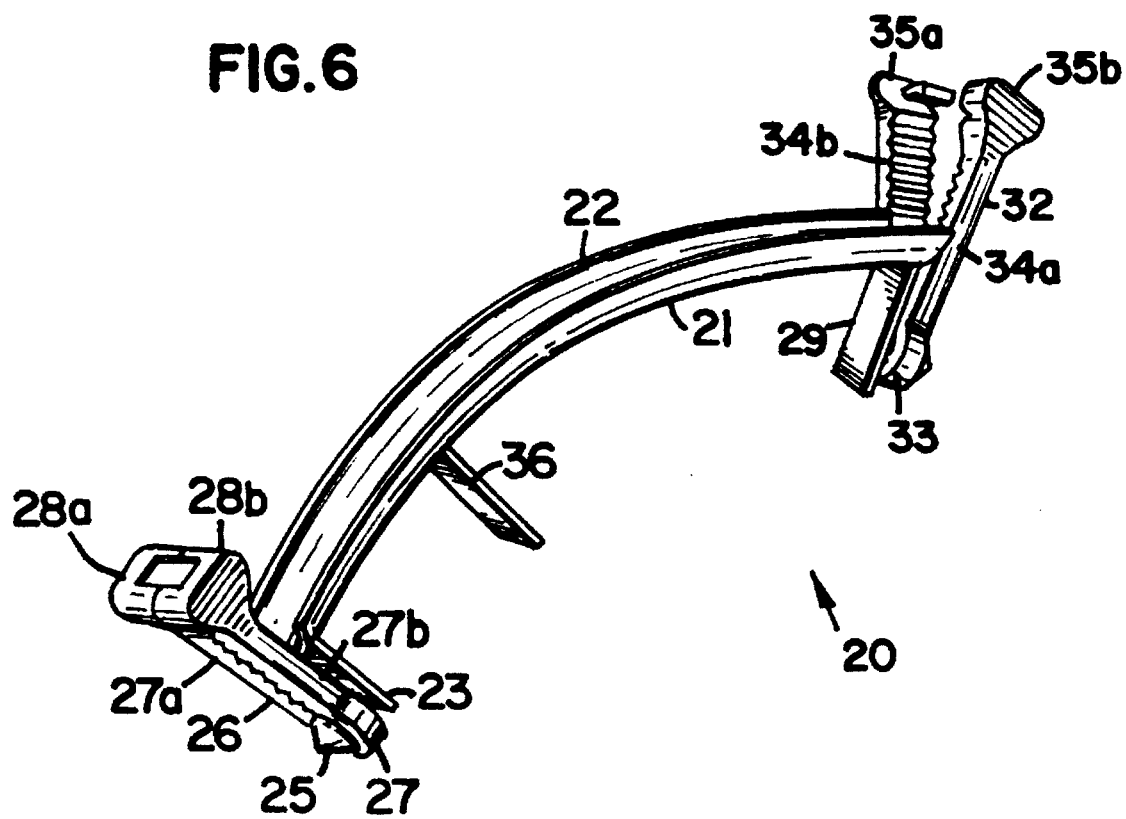

UMBILICAL CORD HOLDER

This application is a continuation-in-part of U.S. patent application Ser. No. 08/095,269, now U.S. Pat. No. 5,372, 581, which was filed on Jul. 21, 1993 and is entitled METHOD AND APPARATUS FOR PLACENTAL BLOOD COLLECTION.

TECHNICAL FIELD

The present invention relates generally to a method and apparatus for withdrawing placental blood from an umbilical vessel prior to the delivery of the placenta and under sterile conditions, and more particularly, to an umbilical cord holder that allows a person to more easily manipulate the umbilical cord and withdraw blood from the umbilical cord vein.

BACKGROUND

Autologous transfusion, that is blood taken from an individual and given back to that same individual at a later time, is a common practice in several surgical specialties. Examples include cardiovascular and orthopedic surgery. In an emergency setting, this process has also been used in the neonatal or newborn population. The interest in finding options to the use of homologous bank blood for the transfusion of premature infants has increased in recent years. An estimated 38,000 premature neonates at or below 1500 grams birth weight are born annually in the United States. Eighty percent of these neonates will require multiple red cell transfusions.

One researcher has calculated that multi-transfused infants are typically exposed to eight different donors. Sacher, Transfus Med Rev 1989;3;39-54. Another researcher has conducted two different studies each of which has determined that 9.5% and 6.2%, respectively, of infants who receive a transfusion actually receive infected blood. Strauss, Transfusion 1989;26:419-22. Concern over the exposure of this population of sick neonates to infectious agents such as HIV; CMV; and Hep A, B and C, have led to the interest in developing options to the use of homologous bank blood in sick, premature infants. These options include using a single donor from a blood bank or a directed family member, using an extended storage media and/or a multi-bag storage system, using recombinant erythropoietin to stimulate the neonates own marrow to manufacture red cells, and using autologous placental blood collected at the time of delivery.

The use of placental blood is promising because the placenta can provide an adequate volume of blood for at least one 10 ml/kg transfusion in 87% of the cases. Sanford Anderson et al., *Retrieval of Placental Blood From the Umbilical Vein to Determine Volume, Sterility, and Presence of Clot Formation*, 146 AJDC 36–39 (January 1992). In addition to the possible use of placental blood for autologous transfusions, researchers are also exploring potential uses of specific elements of placental blood, e.g., removal of the white blood cells for storage and possible future administration to the patient or a relative as an alternative to a bone marrow transplant.

The use of placental blood has had the following limitations: safety of removal; sterility of the blood upon removal and storage; anticoagulation of the blood with the appropriate agent in time to prevent clotting of the specimens; minimizing trauma to the placenta and cord to limit the tissue damage and release of cell contents that might contaminate the placental blood; and efficiency of removal of the blood from the umbilical vessel. In fact, placental blood that is used for transfusion has a bacterial contamination rate of 12%. Sanford Anderson et al., *Retrieval of Placental Blood From the Umbilical Vein to Determine Volume, Sterility, and Presence of Clot Formation*, 146 AJDC 36–39 (January 1992). This bacterial contamination is usually a result of organisms that are on the surface of the umbilical vein.

As described below, elements of the present invention are unique and different from the existing prior art devices in light of the recognition of limitations as enumerated above.

The elimination of bacterial contamination of the placental blood, the need to minimize tissue damage by external forces such as pressure, and the need to properly anticoagulate the placental blood are critical if placental blood is to be used at a later date. The longer a placenta is exposed to the birth canal after the delivery of the infant, and the more manipulation it undergoes during the delivery process or later in a mechanical device, the greater the risk for the above complications to occur. The present invention is an improvement over the Knippscheer et al. device (U.S. Pat. No. 5,053,025) because it is designated to allow withdrawal of the placental blood from the umbilical vessel immediately after the delivery of the infant and before the delivery or manipulation of the placenta while it still resides within the uterus. In addition, the present invention uses the umbilical cord holder to position the umbilical vessel allowing the proper cleansing of its surface and the sterile withdrawal of the placental blood. Unlike the present invention, Knippscheer et al. allows the placental blood to drain from the contamination end of the cut placental cord.

A valve system allows the operator to remove placental blood and mix it with the appropriate volume and type of anticoagulant and transfer that mixture to an appropriate storage bag all within a closed sterile system and with minimal mechanical motion by the operator. This capability is an improvement over the Bonn device (U.S. Pat. No. 5,097,842), which does not allow for variability in volume of blood obtained from infant to infant.

In his research, the applicant has discovered that it is critical to be able to mix the proper amount of anticoagulant with the volume of placental blood that is present. The manipulation of the needle must be minimal or the operator will inadvertently withdraw it from the umbilical vessel allowing loss or contamination of the placental blood. The present invention allows the user to manipulate the umbilical cord and secure the needle relevant to the umbilical vein. It also allows the user to hold the umbilical cord and the valve with a single hand. The user's other hand is then free to efficiently withdraw the placental blood, mix it with an anticoagulant, and store it in a storage bag.

The present invention is also an improvement over Stone's device (U.S. Pat. No. 5,059,168) because of its use of the umbilical cord holder, that allows the user to easily manipulate the umbilical cord and align the needle with the axis of the umbilical vessel to allow one operator to carry out the operation of the placental blood withdrawal. Hamilton (U.S. Pat. No. 3,344,785) and Clarke (U.S. Pat. No. 4,447, 235) both disclose the use of a simple three way stopcock system, which is not sufficient to allow the withdrawal of the placental blood, the admixture of the appropriate anticoagulant, and the transfer of that mixture to a storage bag all within a closed sterile system.

SUMMARY

The present invention is an apparatus and method for the withdrawal of placental blood. It is advantageous because it allow a user to easily manipulate the umbilical cord, it helps maintain the umbilical cord substantially still while the needle is inserted, and it protects the users hand from the needle and thus contamination from the placental blood. More particularly, the present invention has an umbilical cord holder for use while withdrawing placental blood. The umbilical cord holder has a curved trough with a first end, a second end, an open top, and a bottom surface. The trough is needle resistant and sized to hold an umbilical cord. A stem that has first and second ends is operatively connected to the bottom surface of the trough. The stem allows a user to hold and maneuver the umbilical cord holder during use.

The umbilical cord holder is used in conjunction with a needle and a blood collection device by placing the needle-resistant trough in a single hand. An umbilical cord is then placed in the trough wherein the umbilical cord has a cut end and a proximal end that is closer to the placenta than the cut end. The cut end of the umbilical cord is then clamped and the needle is inserted into the umbilical cord. The blood collection device is then operated in order to withdraw blood.

DESCRIPTION OF THE DRAWINGS

FIG. 6 is a perspective view of the umbilical cord holder shown in FIG. 1.

DETAILED DESCRIPTION

Figure 1:
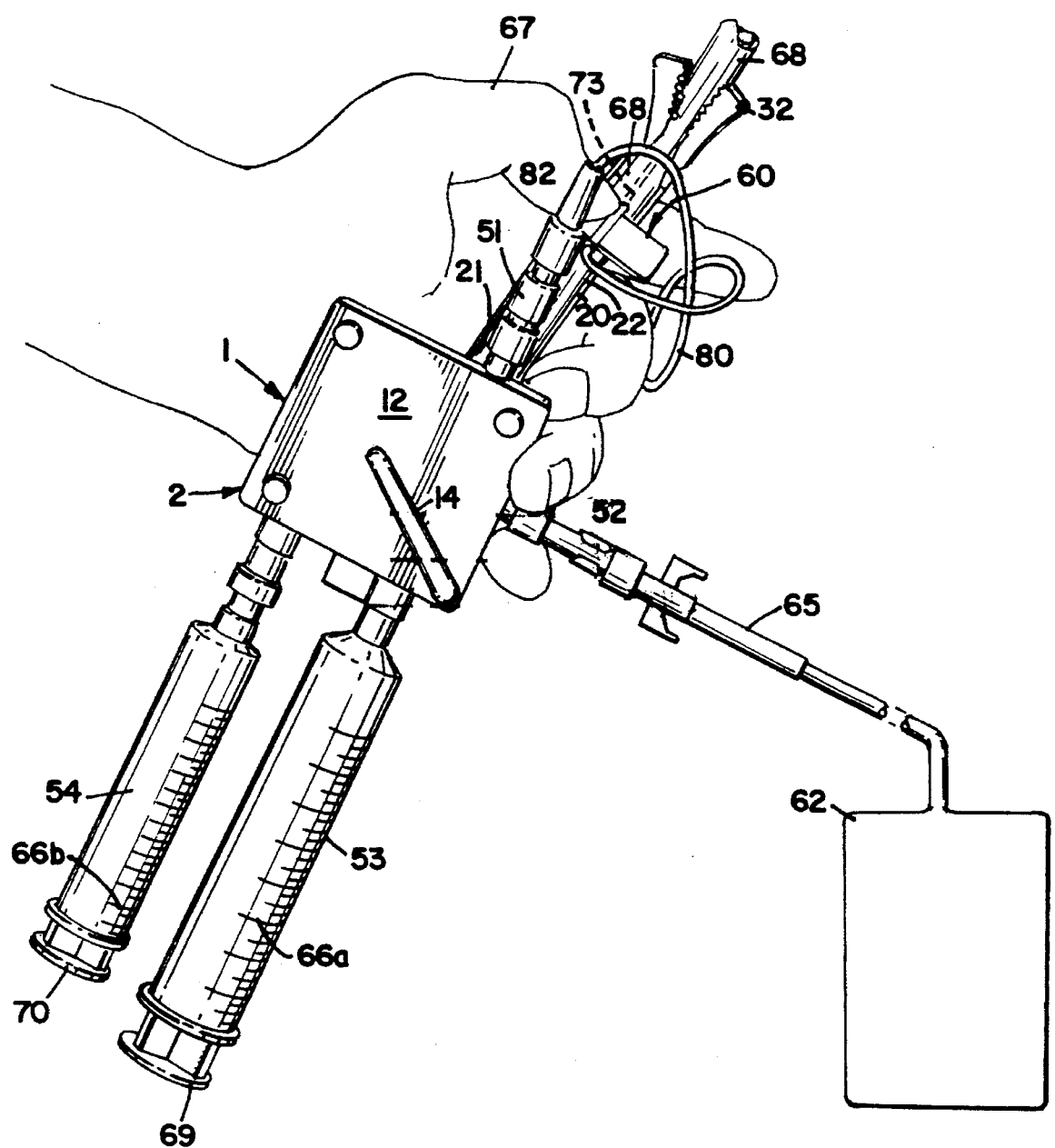
FIG. 1 is a perspective view of the system and method for withdrawing placental blood.

A preferred embodiment of the invention will be described in detail with reference to the drawings, wherein like reference numerals represent like parts and assemblies throughout the several views. Reference to the preferred embodiment does not limit the scope of the invention. The scope of the invention is limited only by the claims, which may be interpreted according to the doctrine of equivalents.

Referring now to the figures, there is illustrated preferred embodiments of the apparatus for placental blood collection that includes the principles of the present invention. Referring to FIGS. 1-5, the apparatus includes a valve, generally shown as 1. The valve includes a housing 2 that has a central cavity 3 that is cylindrical in shape and has a single open end 50. The housing has a first channel 4 that has an outer port 4a and an inner port 4b, a second channel 5 that has an outer port 5a and an inner port 5b, a third channel 6 that has an outer port 6a and an inner port 6b, and a fourth channel 7 that has an outer port 7a and an inner port 7b. Outer ports 4a, 5a, 6a, and 7a all have threads, not shown, capable of receiving mating threads or flanges that are located on syringes, one-way valves, needles, or an orifice on a blood storage bag. Alternately, the components may be glued or otherwise secured to the outer ports.

Figure 2:
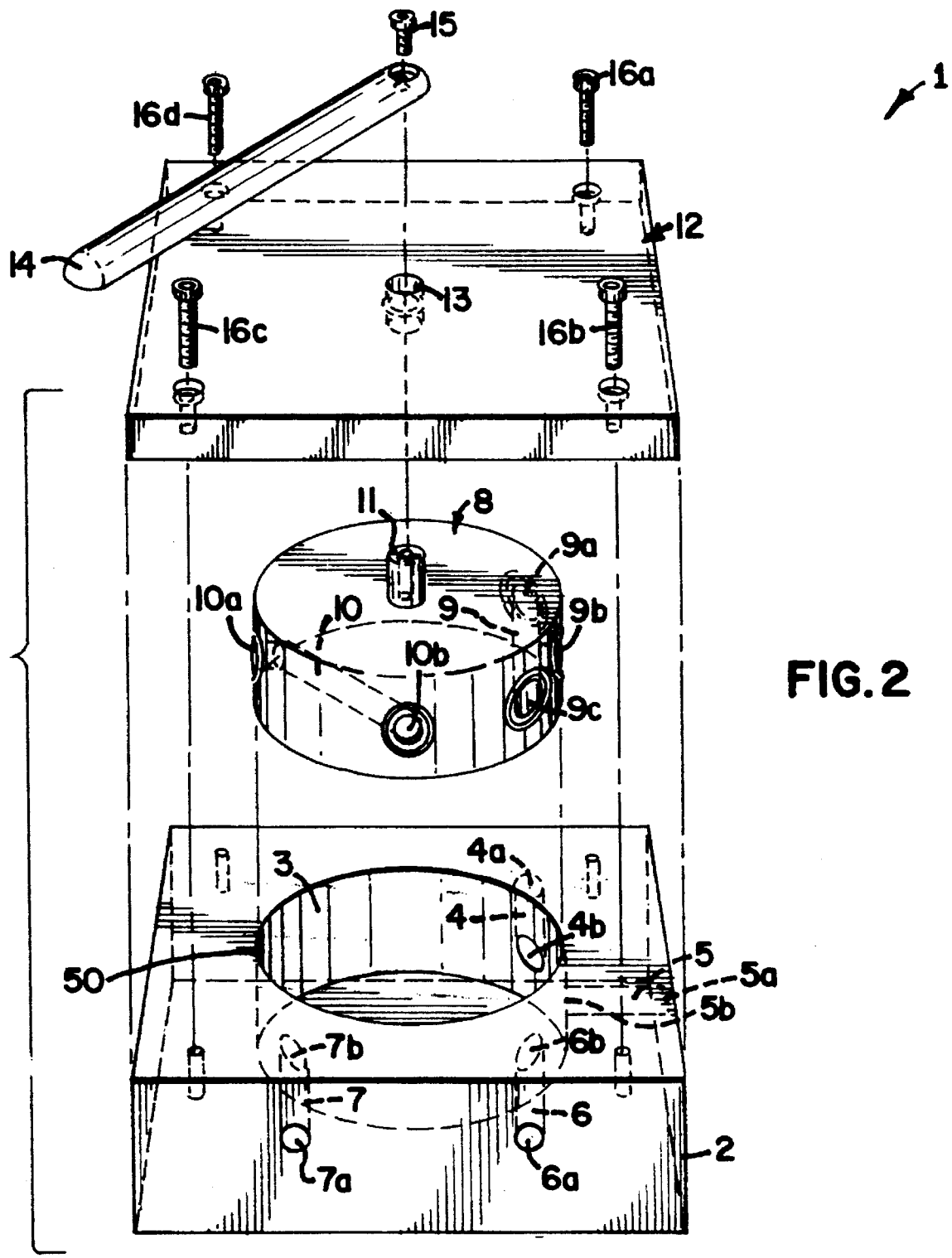
FIG. 2 is an exploded view of the valve shown in FIG. 1 with hidden lines showing the channels.
Figures 3, 7:
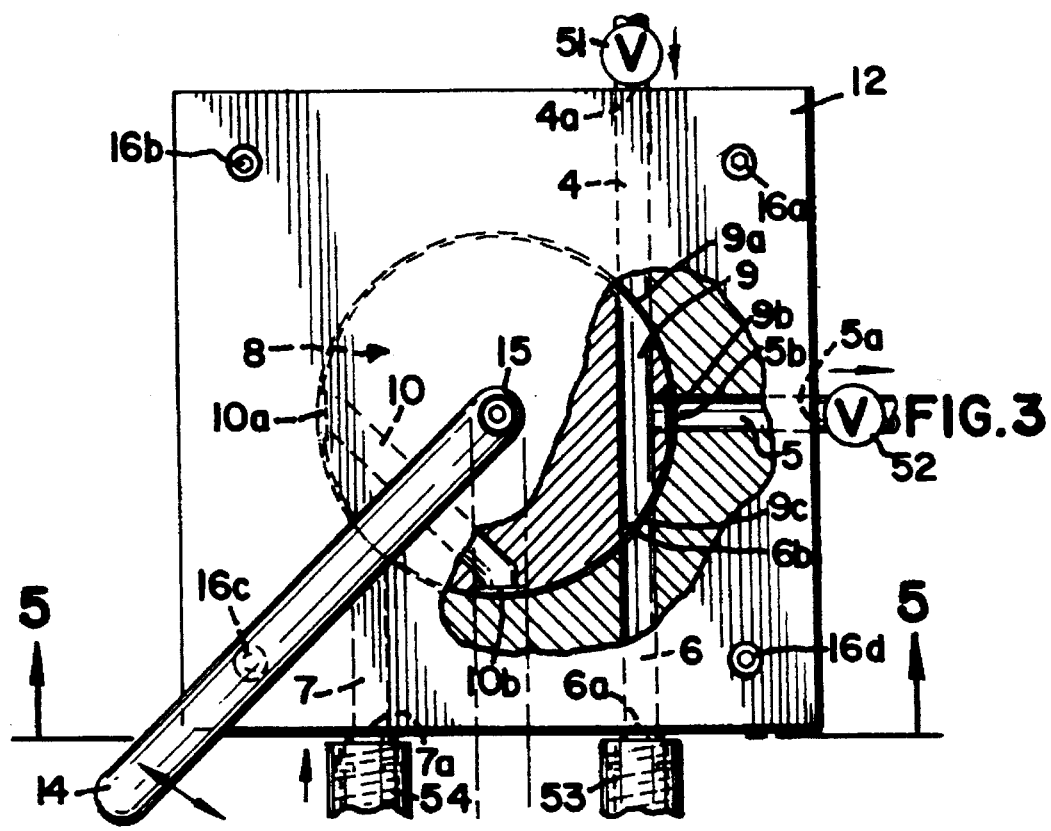
FIG. 3 is a top elevational view of the valve shown in FIG. 1 with the dish in its first position and a break out showing the dish and some channels and hidden lines showing the disk and some channels.
FIG. 7 is a perspective view of the butterfly-type of needle shown in FIG. 1.

Disk 8 is located within cavity 3 and has a diameter that is slightly smaller than the diameter of the cavity 3 so that disk 8 may rotate. Disk 8 has a fifth channel 9 that has a T configuration and three ports 9a, 9b, and 9c. As shown in FIGS. 2 and 3, the fifth channel 9 is oriented in the disk 8 so that when the disk 8 is in a first position, port 9a mates with inner port 4b, port 9b mates with inner port 5b, and port 9c mates with inner port 6b. Disk 8 also includes sixth channel 10 that has two ports 10a and 10b.

Figure 4:
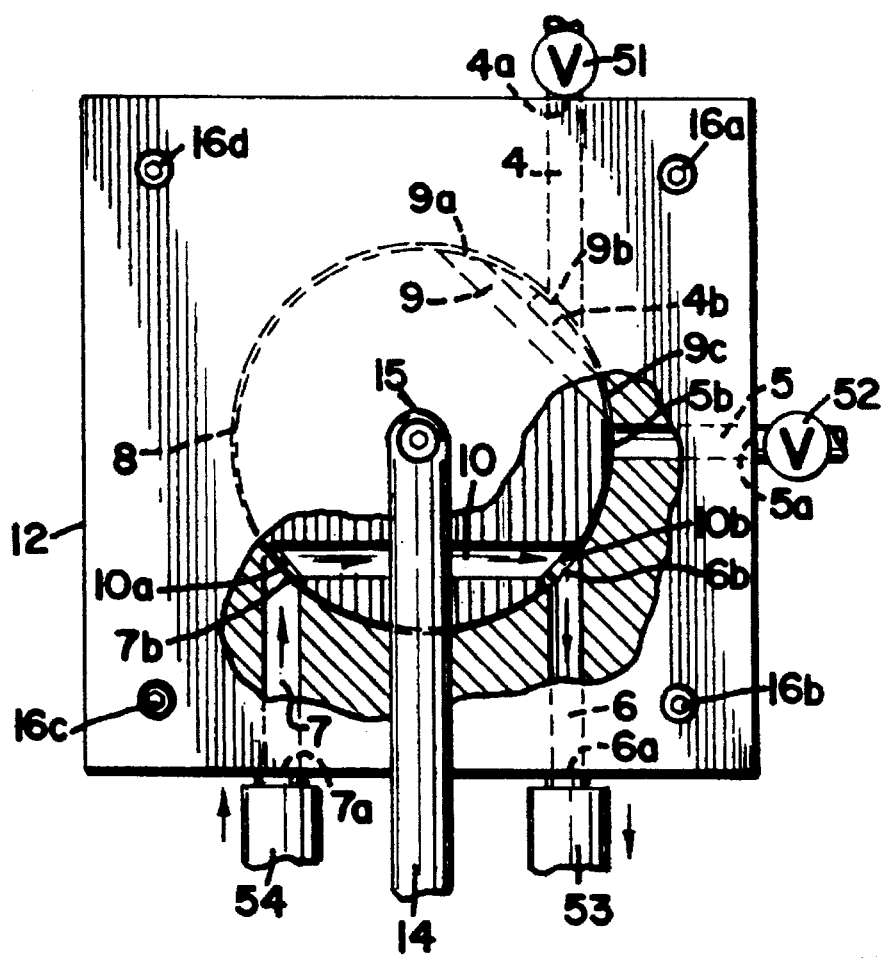
FIG. 4 is a top elevational view of the valve shown in FIG. 1 with the dish in its second position and a break out showing the disk and some channels and hidden lines showing the disk and some channels.
Figure 5:
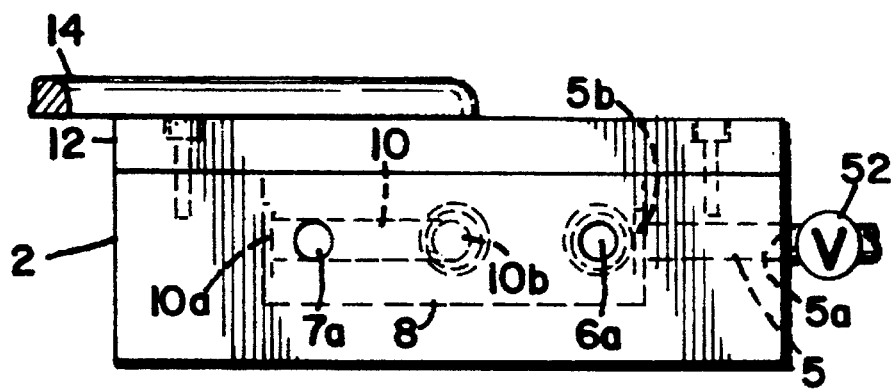
FIG. 5 is a side elevational view of the valve shown in FIG. 1 with hidden lines showing the disk and channels.

When the disk is in a second position, as shown in FIG. 4, sixth channel 10 is oriented so that ports 10a and 10b mate with inner ports 7b and 6b, respectively, and ports 9a, 9b, and 9c are disengaged from inner ports 4b, 5b, and 6b. Finally, disk 8 has a shaft 11 that extends from the top of the disk 8 along its axis. The valve 1 has a plate 12 that covers the cavity 3 and secures the disk 8 within the cavity 3. The plate 12 has a hole 13 through which shaft 11 extends from disk 8. Handle 14 is attached to shaft 11 by screw 15 so that disk 8 rotates as handle 14 is moved from one position to another. Plate 12 is attached to housing 2 by screws 16a, 16b, 16c, and 16d.

As shown in FIG. 1, one-way valve 51 is connected between outer port 4a and butterfly-type needle, generally shown as 60. Butterfly-type needle 60 is described in more detail below. One-way valve 51 is oriented so that fluid may flow from butterfly needle 60 into channel 4, but fluid may not flow from channel 4 back through butterfly needle 60. Butterfly needle 60 is attached to one-way valve 51 by means of threads. In turn, one-way valve 51 is attached to port 4a by means of threads. A second one-way valve 52 is connected between outer port 5a and storage bag 62, which is for storing a blood and anticoagulant mixture. One-way valve 52 is oriented so that fluid may flow into the storage bag 62, but fluid may not flow from the storage bag 62 back into channel 5. Storage bag 62 has a tube 65 that fits around a port on one-way valve 52. In turn, one-way valve 52 is attached to outer port 5a by means of threads. Preferably, one-way valves 51 and 52 are model number BC-1000 manufactured by Burron Medical, Inc. of 824 12th Avenue, Bethlehem, Pa. 18018.

Finally, blood collection syringe 53 is attached to outer port 6a and anticoagulant syringe 54 is attached to outer port 7a. Blood collection syringe 53 and anticoagulant syringe 54 both include indicia of measurement 66a and 66b, respectively. Additionally, blood collection syringe 53 and anticoagulant syringe 54 include threads, not shown, that are capable of mating with the threads of outer ports 6a and 7a.

In FIG. 6, an umbilical cord holder is shown generally as 20. The umbilical cord holder 20 has a curved trough 21 that has an open top 22. Curved trough 21 is made of a needle resistant material such as stainless steel, which can be sterilized. A flange 23 extends downward from the first end of the trough 21 and is attached by suitable means such as a weld. A shaft, not shown, extends outward from flange 23 and has a cap 25. The shaft, not shown, and cap 25 are preferably a rivet that is easily secured to flange 23. Cut-end umbilical cord clamp 26 has a curved end 27 that snap locks around the shaft. Cut-end umbilical cord clamp 26 also has clamping portions 27a and 27b. The inside surfaces of clamping portions 27a and 27b is lined with small ribs. Finally, clamp 26 has a fastener with a male end 28a and a female end 28b mounted at the end of clamping portion 27a and 27b, respectively. The opposite end of the trough 21 has an identical clamping mechanism that is comprised of flange 29, uncut-end umbilical cord clamp 32, circular end 33, clamping portions 34a and 34b, male fastener 35a, and female fastener 35b. This opposite end also has a rivet, not shown, that forms a shaft and a cap. Preferably, clamps 26 and 32 are model number 31-041 Cord Clamp manufactured by Qualtex, a division of De Royal Industries, Inc., of Powell, Tenn. 37849. Stem 36 extends downward from trough 21 and is located at a distance from cut-end umbilical clamp 26 and flange 23 sufficient to allow a person to insert their little finger between flange 23 and stem 36.

As shown in FIG. 7, butterfly-type needle 60 includes a hollow needle 73, a first flange 72, and a second flange 74. First flange 72 and second flange 74 are operatively connected to oppositely disposed sides of needle 70. Needle 70 has a tip 76 and a base 78. Tube 80 has a first end connected to base 78 of needle 70 and a second end that is connected to coupling 82. Coupling 82 is attachable to one-way valve 51. The preferred butterfly-type of needle is Model No. 4590 manufactured by Abbott Laboratories of North Chicago, Ill. 60064.

As shown in FIG. 1, in order to collect placental blood, the umbilical cord holder 20 is placed in a first hand 67 such that the stem 36 is located between the little and fourth fingers. The curved trough 21 then lays along the base of the fingers and adjacent to the palm. The stem allows the umbilical cord holder 20 to be easily grasped and maneuvered. The other hand, not shown, is then available to clamp the umbilical cord 68, manipulate devices such as the syringes 53 and 54, and perform other surgical procedures. The umbilical cord 68 is then placed in trough 21 so that the umbilical cord 68 extends from the placenta through uncut-end umbilical cord clamp 32, the trough 21, and the cut-end clamp 26. Clamping portions 27a and 27b of cut-end clamp 26 are then squeezed together so that male and female fasteners 28a and 28b secure together thereby restricting the umbilical cord. The umbilical cord is then cleansed by a suitable antibacterial agent. After the umbilical cord is properly cleaned, needle 70 is inserted into a vein of the umbilical cord.

After the hollow needle 73 is inserted into the umbilical vein, either the first flange 72 or the second flange 74 is placed against one edge of the trough 21. The user can then rest his/her thumb on top of the flange 72 or 74 and hold the hollow needle 73 in axial alignment with the umbilical vein. This operation is important because a movement in the user's first had 67 would otherwise cause the hollow needle 73 move out of axial alignment with the umbilical vein and restrict the flow of blood through the hollow needle 73.

After hollow needle 73 is inserted into the umbilical cord, valve 1 is set in the first hand 67 so that it is gripped between the base of the palm and the finger tips. Holding valve 1 and the umbilical cord holder 20 in this manner allows the user to keep his/her second hand, not shown, free to continue surgical procedures.

The disk 8 then must be oriented in its first position so that port 9a is aligned with inner port 4b, port 9b is aligned with inner port 5b, and port 9c is aligned with inner port 6b. The plunger 69 of the blood collection syringe 53 is then withdrawn thereby causing blood to flow from the placenta through a vein in the umbilical cord, the needle 60, the one-way valve 51, the first channel 4, the fifth channel 9, the third channel 6, and into the blood collection syringe 53. Handle 14 is then turned so that disk 8 rotates into its second position and causes the fifth channel 9 to disengage and the sixth channel 10 to engage so that port 10a is aligned with inner port 7a and port 10b is aligned with inner port 6b. The plunger 70 on the anticoagulant syringe 54 is then depressed thereby causing the anticoagulant to flow from the anticoagulant syringe through the fourth channel 7, through the sixth channel 10, through the third channel 6, and into the blood collecting syringe 53 thereby causing the blood and the anticoagulant to mix.

Handle 14 is then rotated in order to return disk 8 to its first position. As a result, ports 9c, 9b, and 9a mate with inner ports 6b, 5b, and 4b, respectively. The plunger 69 of the blood collection syringe 53 is then depressed, which causes the blood and anticoagulant mixture to flow through the third channel 6, through the fifth channel 9, through the second channel 5, through one-way valve 52, and into the storage bag 62. One-way valve 51 prevents the blood and anticoagulant mixture from flowing back through needle 60 into the umbilical cord 68.

The procedure described above may be repeated until the desired volume of placental blood is stored in the bag 62. After the necessary amount of blood is withdrawn from the placenta, the uncut-end umbilical cord clamp 32 is closed.

One skilled in the art will realize that a stopcock system as well as other types of valves can be used in place of valve 1. One skilled in the art will further realize that the umbilical cord holder might be useful in conjunction with other types of medical equipment.

It is apparent from the description set forth above that the holder 20 has several functions. It helps the user manipulate the umbilical cord in order to get the hollow needle 73 in axial alignment with the umbilical vein. The umbilical cord holder 20 also maintains the umbilical cord substantially still while the user is inserting the hollow needle 73. Additionally, the holder 20 prevents the needle from passing through the umbilical cord and pricking the user's hand. Thus, holder 20 helps protect the user from injury and from potentially contaminated placental blood.

While the invention has been described in conjunction with a specific embodiment thereof, it is evident that different alternatives, modifications, and variations will be apparent to those skilled in the art in view of the foregoing description. Accordingly, the invention is not limited to these embodiments or the use of elements having specific configurations and shapes as presented herein.

The invention that I claim is:

1. An umbilical cord holder for use while withdrawing placental blood, the umbilical cord holder comprising:

(a) a trough having a first end, a second end, an open top, and a bottom surface, the trough being resistant to puncture by a needle and sized to hold an umbilical cord;

(b) a stem having first and second ends, the first end operatively connected to the bottom surface, wherein the stem allows a user to hold and maneuver the umbilical cord holder during use; and (c) a first clamp operably connected to the first end of the trough, the first clamp capable of constricting a region of the umbilical cord so that the fluid cannot pass through the constricted region.

2. The apparatus of claim 1 further comprising a second clamp operably connected to the second end of the curved trough, the second clamp capable of constricting a region of the umbilical cord so that fluid cannot pass through the constricted region.

3. A combination umbilical cord holder and hollow needle for use while withdrawing placental blood, the umbilical cord holder comprising:

(a) a trough having a first end, a second end, an open top, and a bottom surface, the trough being resistant to puncture by a needle and sized to hold an umbilical cord;

(b) a stem having first and second ends, the first end operatively connected to the bottom surface, wherein the stem allows a user to hold and maneuver the umbilical cord holder during use;

(c) a first clamp operably connected to the first end of the trough, the first clamp capable of constricting a region of the umbilical cord so that fluid cannot pass through the constricted region;

(d) a second clamp operably connected to the second end of the trough, the second clamp capable of constricting a region of the umbilical cord so that fluid cannot pass through the constricted region;

(e) a hollow needle through which blood can flow; and (f) a flange operably connected to the hollow needle, the flange for resting against the trough whereby the hollow needle is stabilized relative to the umbilical cord.

4. An umbilical cord holder for use while withdrawing placental blood, the umbilical cord holder comprising:

(a) a trough having a first end, a second end, an open top, and a bottom surface, the trough being resistant to puncture by a needle and sized to hold an umbilical cord;

(b) a stem having first and second ends, the first end operatively connected to the bottom surface, wherein the stem allows a user to hold and maneuver the umbilical cord holder during use;

(c) a first clamp operably connected to the first end of the trough, the first clamp capable of constricting a region of the umbilical cord so that fluid cannot pass through the constricted region; and (d) a second clamp operably connected to the second end of the trough, the second clamp capable of constricting a region of the umbilical cord so that fluid cannot pass through the constricted region.

5. An umbilical cord holder for use while withdrawing placental blood, the umbilical cord holder comprising:

(a) a trough having a first end, middle section, a second end, an open top, and a bottom surface, the trough being resistant to puncture by a needle and sized to hold an umbilical cord;

(b) the middle section of the trough being raised higher than the first and second ends, thereby the trough being arcuate from its first end to its second end; and (c) a stem having first and second ends, the first end operatively connected to the bottom surface, wherein the stem allows a user to hold and maneuver the umbilical cord holder during use.

6. The apparatus of claim 5 further comprising a first clamp operably connected to the first end of the trough, the first clamp capable of constricting a region of the umbilical cord so that fluid cannot pass through the constricted region.

7. The apparatus of claim 6 further comprising a second clamp operably connected to the second end of the trough, the second clamp capable of constricting a region of the umbilical cord so that fluid cannot pass through the constricted region.

* * * * *